United States Patent
Grenfell et al.

(10) Patent No.: US 7,715,982 B2
(45) Date of Patent: *May 11, 2010

(54) MONITORING SPORTS

(75) Inventors: Ronald Grenfell, Melbourne (AU); Kefei Zhang, Melbourne (AU); Colin Mackintosh, Bruce (AU); Daniel James, Nathan (AU); Neil Davey, Nathan (AU)

(73) Assignees: M.B.T.L. Limited, Hawthorn (AU); Sportzco Pty Ltd, Hawthorn (AU)

( * ) Notice: Subject to any disclaimer, the term of this patent is extended or adjusted under 35 U.S.C. 154(b) by 90 days.

This patent is subject to a terminal disclaimer.

(21) Appl. No.: 11/843,077

(22) Filed: Aug. 22, 2007

(65) Prior Publication Data

US 2008/0046179 A1 Feb. 21, 2008

Related U.S. Application Data

(63) Continuation-in-part of application No. 10/531,263, filed on Apr. 13, 2005, now Pat. No. 7,272,499.

(30) Foreign Application Priority Data

Sep. 28, 2006 (AU) ............................... 2006222730
Sep. 28, 2006 (AU) ............................... 2006222732

(51) Int. Cl.
*G06F 7/00* (2006.01)

(52) U.S. Cl. ..................... 701/213; 701/25; 701/207; 702/182

(58) Field of Classification Search ............... 701/211, 701/213, 214, 207, 25; 340/427, 432; 482/57; 702/182, 188
See application file for complete search history.

(56) References Cited

U.S. PATENT DOCUMENTS

| | | | |
|---|---|---|---|
| 4,984,986 A | 1/1991 | Vohnout | |
| 5,099,589 A | 3/1992 | Lai et al. | |
| 6,148,262 A | 11/2000 | Fry | |
| 6,308,649 B1 | 10/2001 | Gedeon et al. | |
| 7,272,499 B2 * | 9/2007 | Grenfell et al. | ............ 701/213 |

* cited by examiner

*Primary Examiner*—Gertrude Arthur Jeanglaud
(74) *Attorney, Agent, or Firm*—Connolly Bove Lodge & Hutz LLP

(57) ABSTRACT

A data logger for a monitoring sports which includes an accelerometer, a GPS unit to sense position and velocity, a heart rate monitor, a controller programmed to manipulate the data and provide a display of the heart rate, speed, and other sport parameters. The data can be stored or transmitted to a remote computer for use by the coach. The device is useful in football codes, athletics, snow sports and cycling.

8 Claims, 16 Drawing Sheets

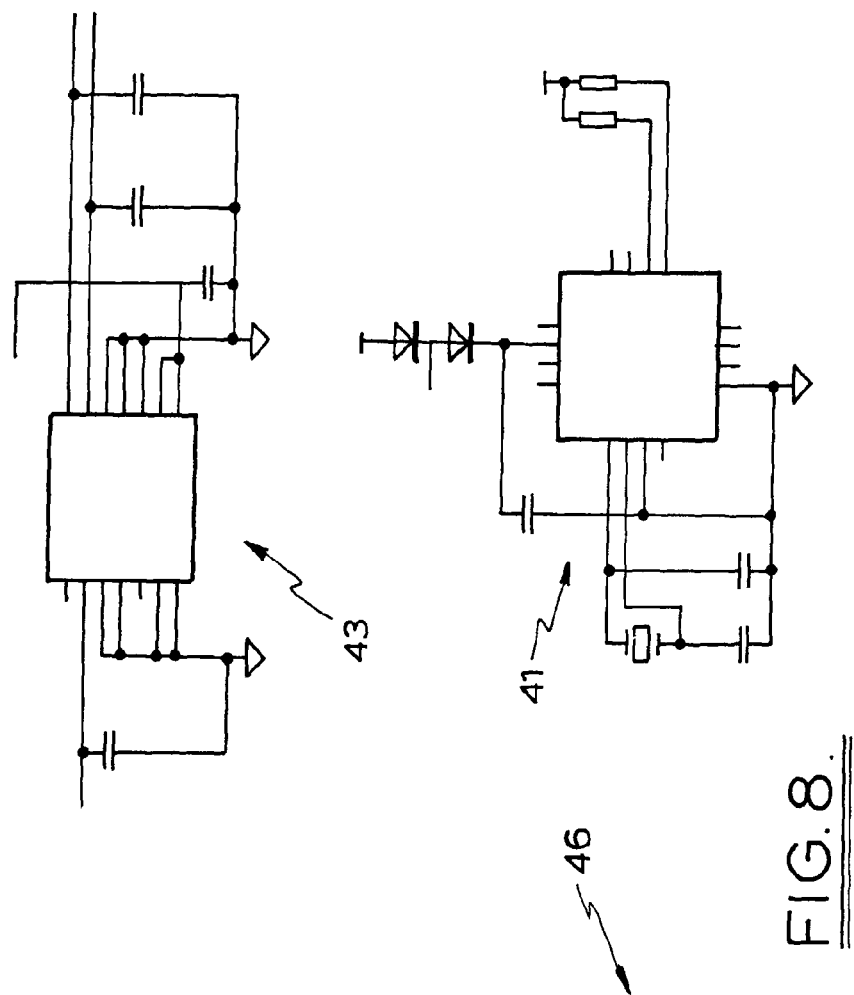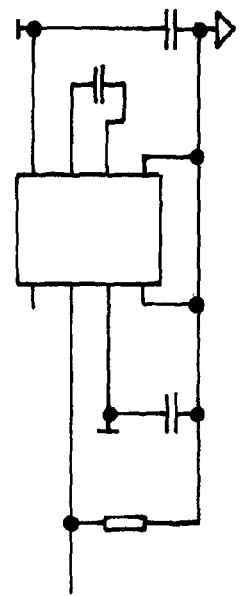
FIG. 8.

MONITORING SPORTS

This application is a Continuation-in-Part of co-pending application Ser. No. 10/531,263, filed on Apr. 13, 2005, now U.S. Pat. No. 7,272,499, and for which priority is claimed under 35 U.S.C. 120; and this application claims priority of Application No. 2006222732 filed in Australia on Sep. 28, 2006; Application No. 2003903123 filed in Australia on Jun. 23, 2003; and Application No. 2002952407 filed in Australia on Nov. 1, 2002, under 35 U.S.C. 119. The entire contents of these applications are hereby incorporated by reference.

This invention relates to a method and system for monitoring performance characteristics of athletes and in particular the particular movements which contribute to enhanced performance.

BACKGROUND TO THE INVENTION

Monitoring of athletes performance both in training and in competition is important in the development and implementation of new approaches aimed at improving sporting performance.

The ability to measure and record athlete physiological information and positional information associated with athlete movement in real-time is critical in the process of athlete training and coaching. Blood oxygen, respiration, heart rates, velocity, acceleration/force, changes in direction, and position and many other factors are required in elite athlete training and coaching. The position, movement and force information plays an important role in effective analysis of the athlete performance, especially for rowers. For example, the stroke frequency, force and synchronisation of athletes are critical for the performance of the rowers in a competition. Currently the stroke information can only be measured in either dedicated sports laboratories or using simulated devices. Reliable analysis of the stroke rate and stroke distance in rowing has been a challenge for a long time due to the availability of the real scenario data, in particular a high precision of position, velocity and acceleration data. Existing technologies used for this purpose include theoretical studies, video-footage procedure, indoor tank procedure, computer modelling and ergometer studies. Much of the equipment is either too heavy, expensive, obtrusive or less reliable. Therefore, smart real-time monitoring during training and competition to help elite athletes to improve their performance and avoid injuries is critical for both athletes and coaches. Any methodology that would improve the situation would not only bring benefits to the rower practice, but also to many other sports related application including both team sports and individual athlete.

U.S. Pat. Nos. 4,984,986 and 5,099,689 disclose measuring systems for off water rowing apparatus which measure the number of strokes or the force applied to the machine.

U.S. Pat. No. 6,308,649 discloses a monitoring system for sail boat racing which provides feedback to the crew of such parameters as wind speed and direction boat speed, sail boat comfort parameters, sail shape, line tensions, rudder angle etc.

Some development of monitoring systems has occurred in non water sports. U.S. Pat. No. 6,148,262 discloses a bike mounted sports computer including a GPS receiver to provide a mapping facility.

In athletics the ability to monitor movement, acceleration and rhythm is useful in especially in track and field events. In team games such as football the ability to track and log the movements of players is useful to coaches.

It is an object of this invention to provide a device for real time monitoring of both boat and athlete performance in on water events and in athletics and other sports.

BRIEF DESCRIPTION OF THE INVENTION

To this end the present invention provides a data acquisition system for use in sporting events which incorporates
 a) a global position sensor to derive 3 dimensional positioning data relative to time elapse
 b) at least one accelerometer to derive acceleration and velocity data in 3 dimensions
 c) a microcontroller with a clock to interrogate the global position sensor at a frequency of at least 1 Hz and to measure the accelerometer data
 d) a power supply
 e) communication means for transmission of global position and accelerometer data from the microcontroller to a computer device
 f) said computer device being programmed to use the global position and accelerometer data to provide accurate and continuous output of parameters such as velocity acceleration and distance traveled.

This device will provide longitudinal data from the training and competition environment and provide both athlete physiological data and performance data related to the sport.

For rowing or other on water sports the movement sensor data may be used to produce out puts that correlate to
 a) boat speed
 b) acceleration or force for each stroke
 c) stroke rate The movement sensor is an accelerometer or gyrosensor combined with a GPS unit to sense instantaneous position and velocity. A GPS receiver transmitter is included in the device to derive location and speed parameters.

Preferably physiological sensors are also attached to the athlete and integrated with the sensor system. Heart rate is the prime parameter to be measured and this may be sensed using electrical sensors or microphones. Respiratory rate is also important and may be measured by sensing the stretching of a chest band or using a microphone and signal recognition software. Another parameter is arterial oxygen saturation which may be measured non invasively by a sensor, placed on an earlobe or finger tip, using pulse oximetry employing an infra red absorption technique. Infra-red spectroscopy may be used for non invasive measurement of blood lactate concentrations.

Preferably velocity is derived from the global position sensor and the accelerometer data is sampled to obtain movement characteristics of the sport being monitored. Preferably the accelerometer data is integrated to derive velocity related movement characteristics and drift is checked every second using the output from the global position sensor.

This system provides a platform device which can be used for a wide range of sports simply by providing appropriate software to derive from the accelerometer and GPS data, the desired sport parameters such as stride frequency velocity stride length, vertical acceleration, time off the ground for long jumping and events such as aerial skiing. An alternative sensor to accelerometers is a gyrosensor which may also be used in addition to the accelerometers. The gyrosensor is able to sense movements like strokes and turns in swimming or strides and loft time in running, in a similar fashion to accelerometers. Additionally these sensors can indicate direction of the movement.

The system of this invention can be used in swimming to identify stroke type, turns, and with turns the number of laps and the stroke rate per lap as well as lap times. Careful analysis of each stroke can show the efficiency and power by comparing the acceleration and deceleration cycles and the effect of breathing cycles. In open water swimming the GPS can also be used to provide an indication of location, direction, and speed relative to the course.

The system of this invention can be used in cycling to identify location, speed, power and heart rate. By adding a magnetometer to the unit on the cyclist pedal cadence can be sensed. Alternatively pedal cadence can be sensed by a unit on the bike and transferred to the unit on the cyclist using a radio frequency pickup unit.

In skiing the unit can detect velocity, position, and heart rate but also the power imparted by each leg and the lateral acceleration and deceleration. In jumping the unit can detect loft time and speed.

In team sports such as the various codes of football the movement of the player can be tracked and the direction and force of a kick can be detected.

DETAILED DESCRIPTION OF THE INVENTION

Particular embodiments of the invention will be described.

Figure 6:
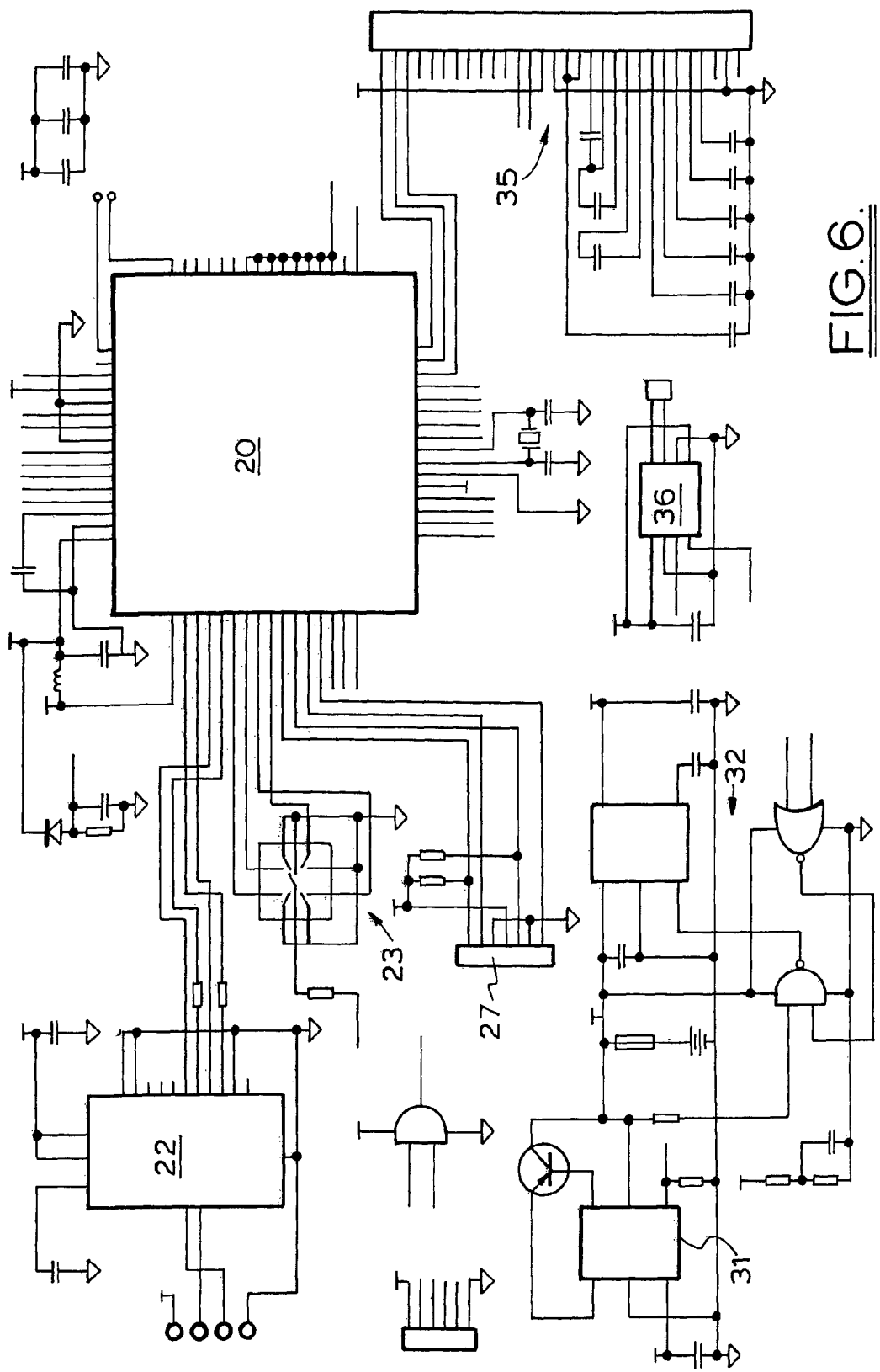
Figure 7:
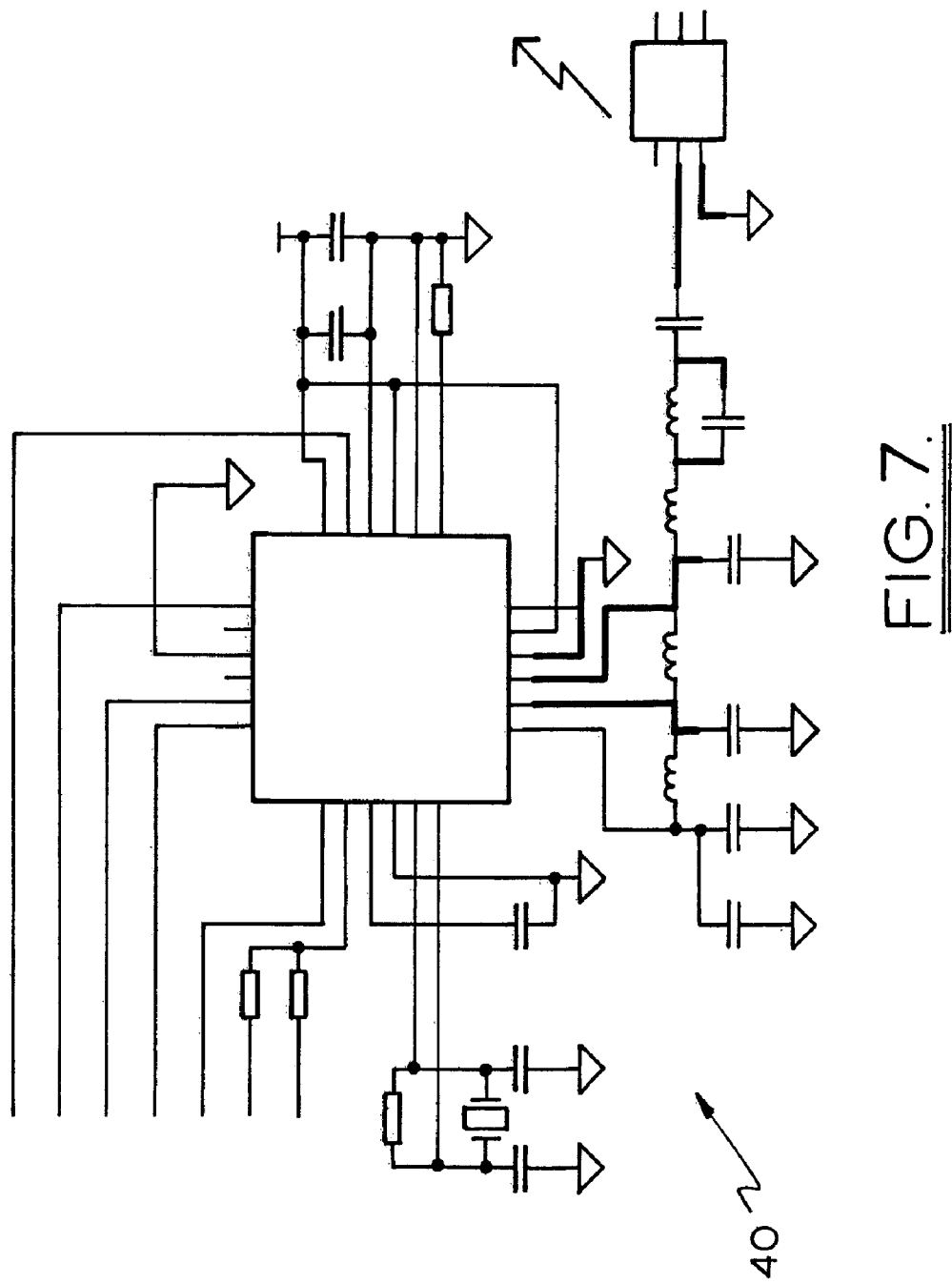
Figure 9:
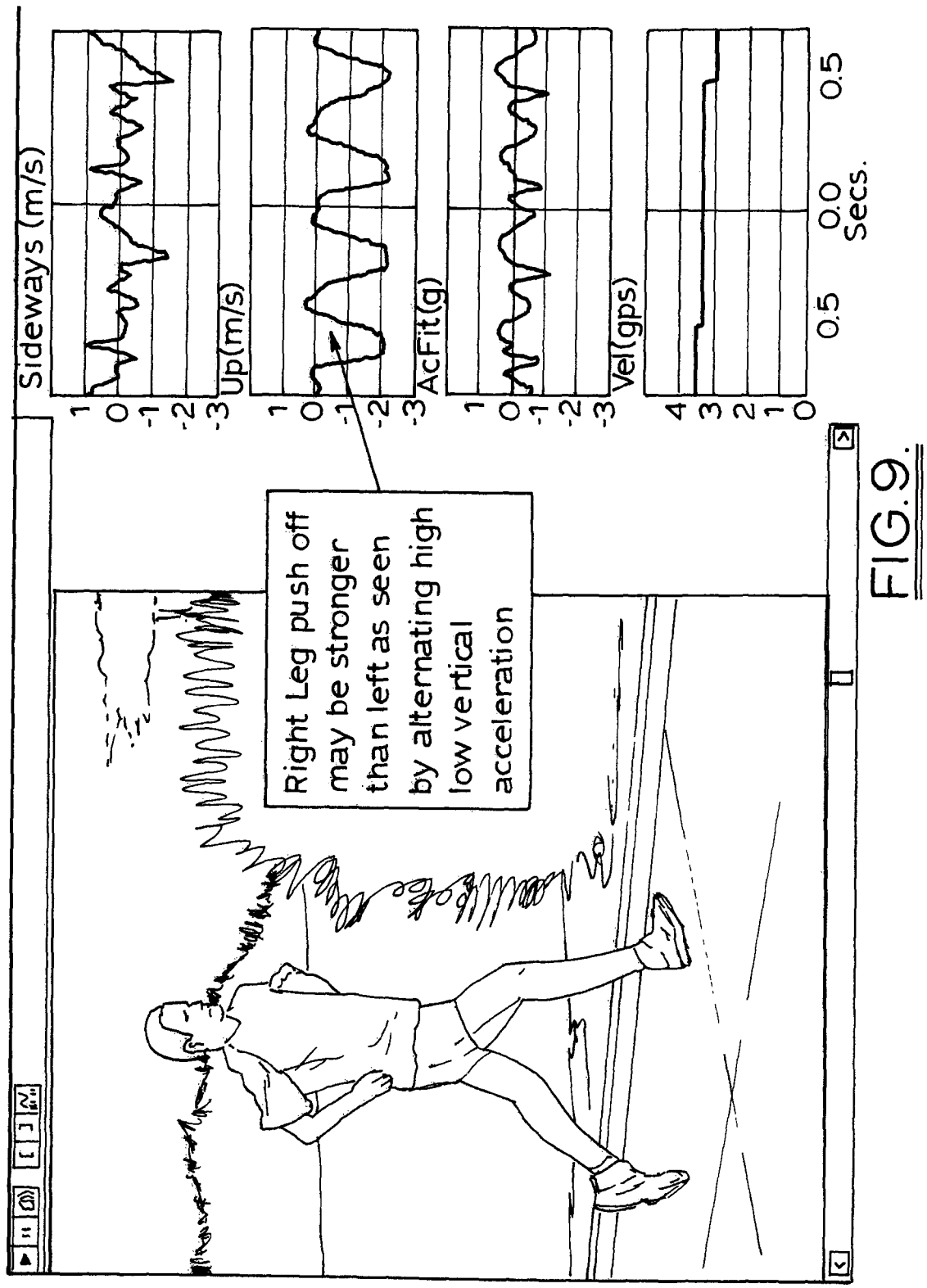
Figure 10:
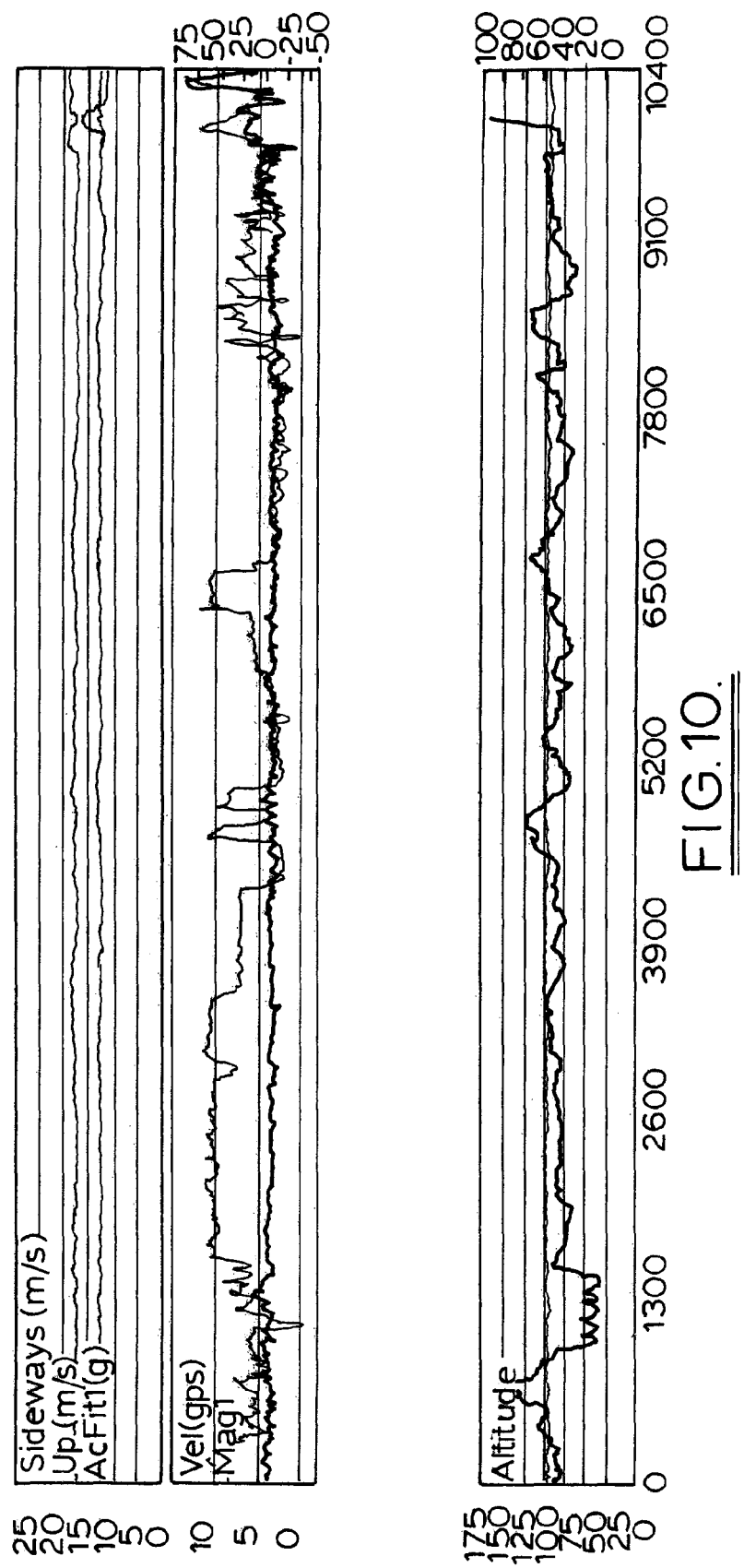
Figure 11:
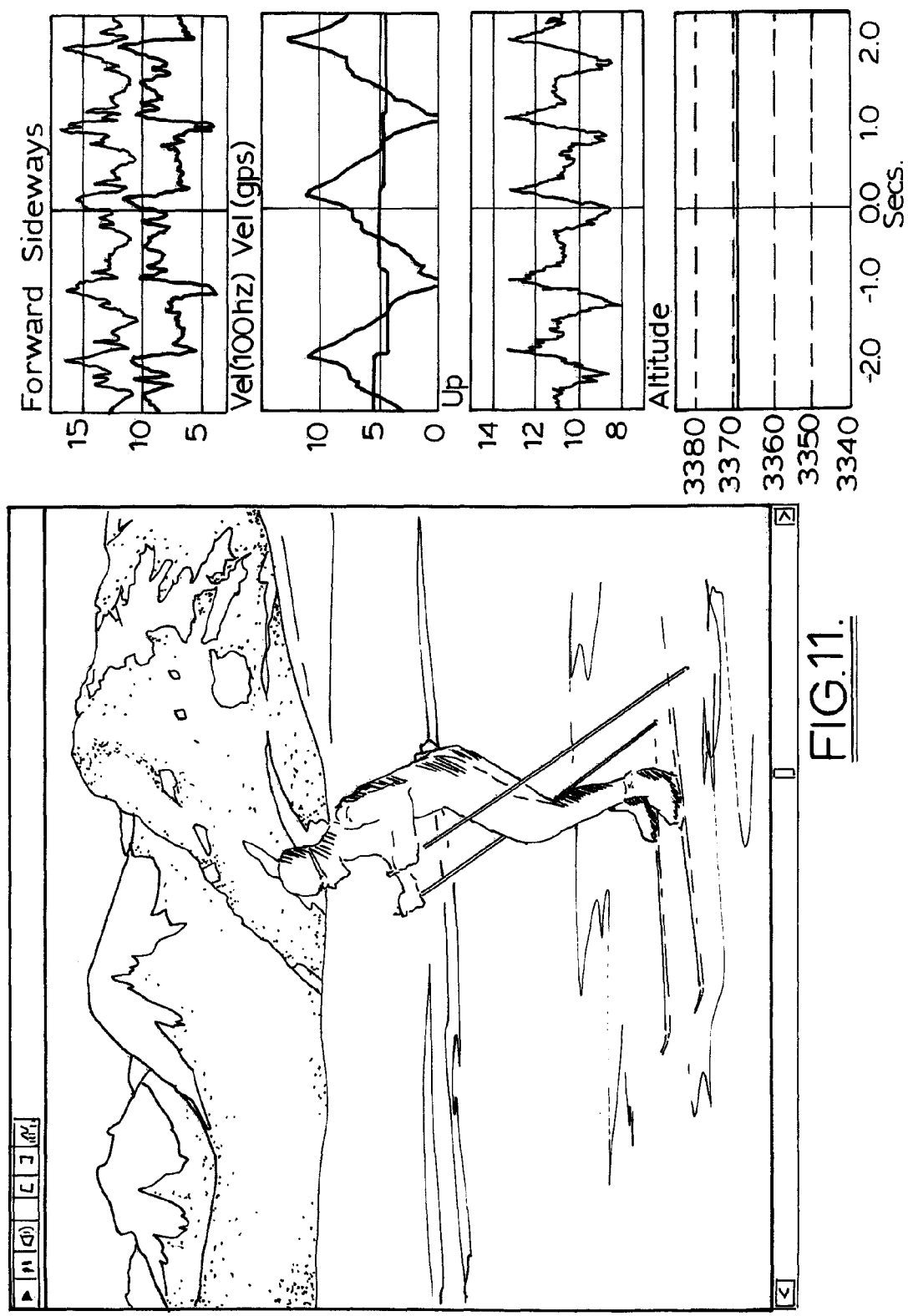
Figure 12:
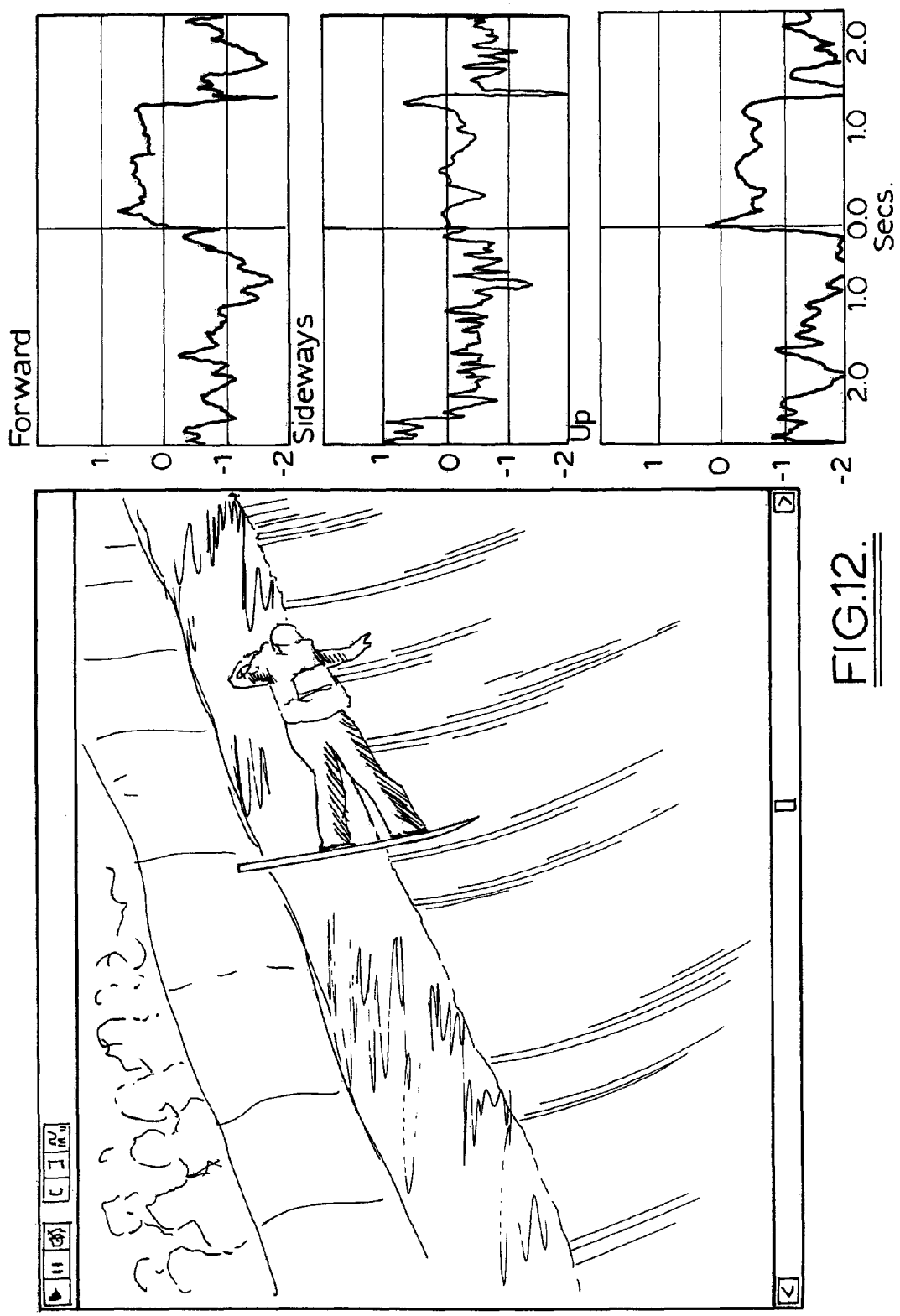
Figure 13:
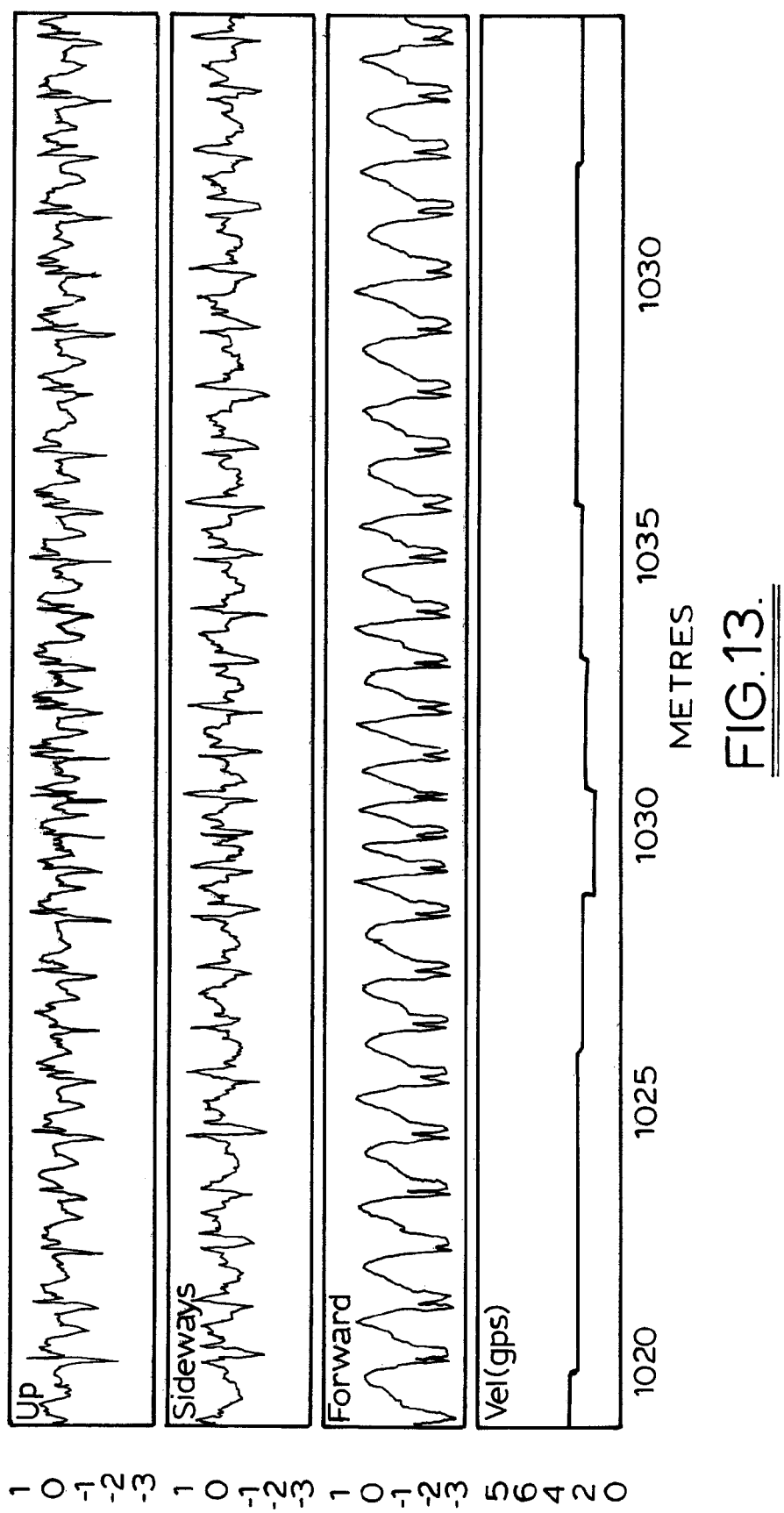
Figure 14:
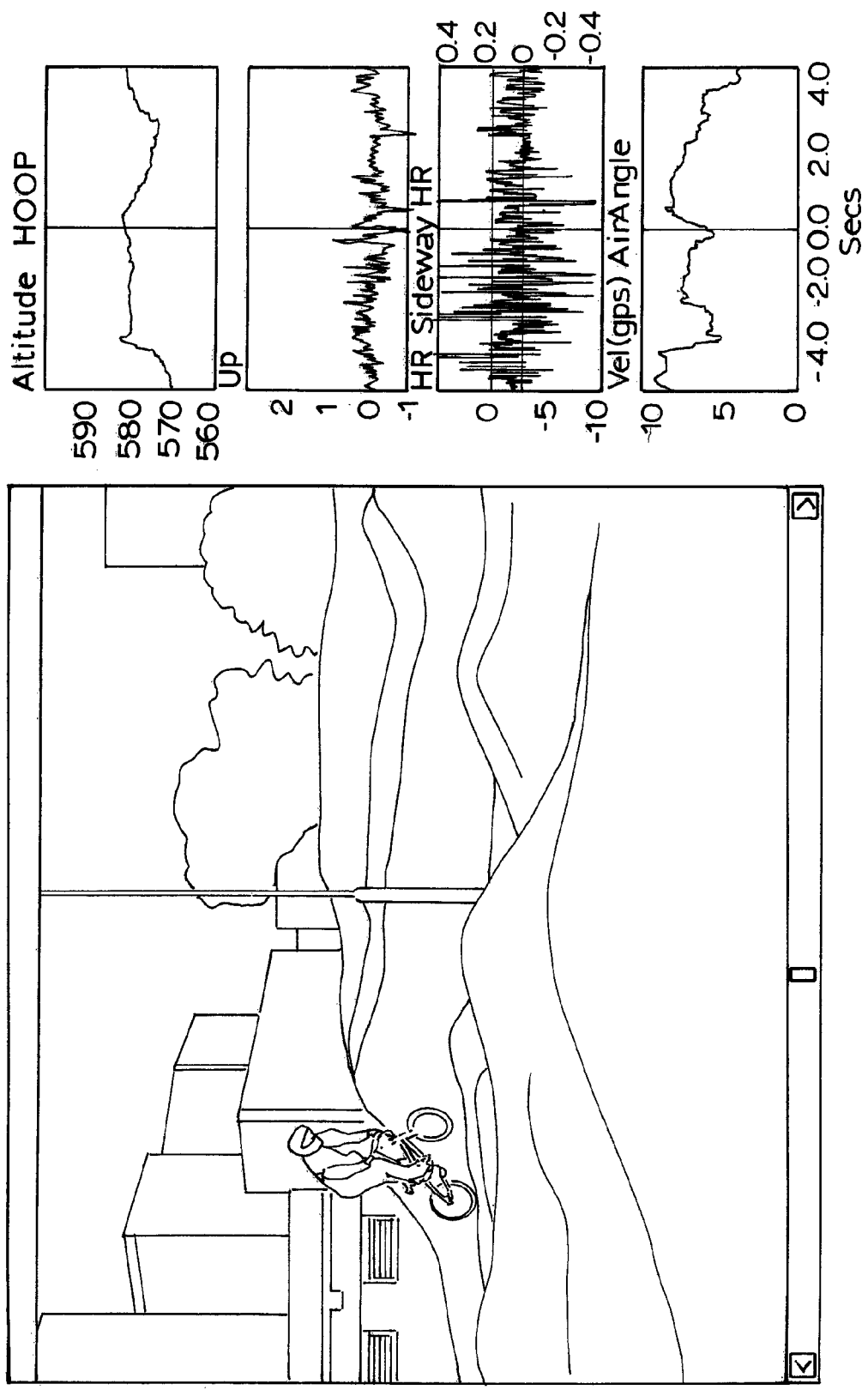
Figure 15:
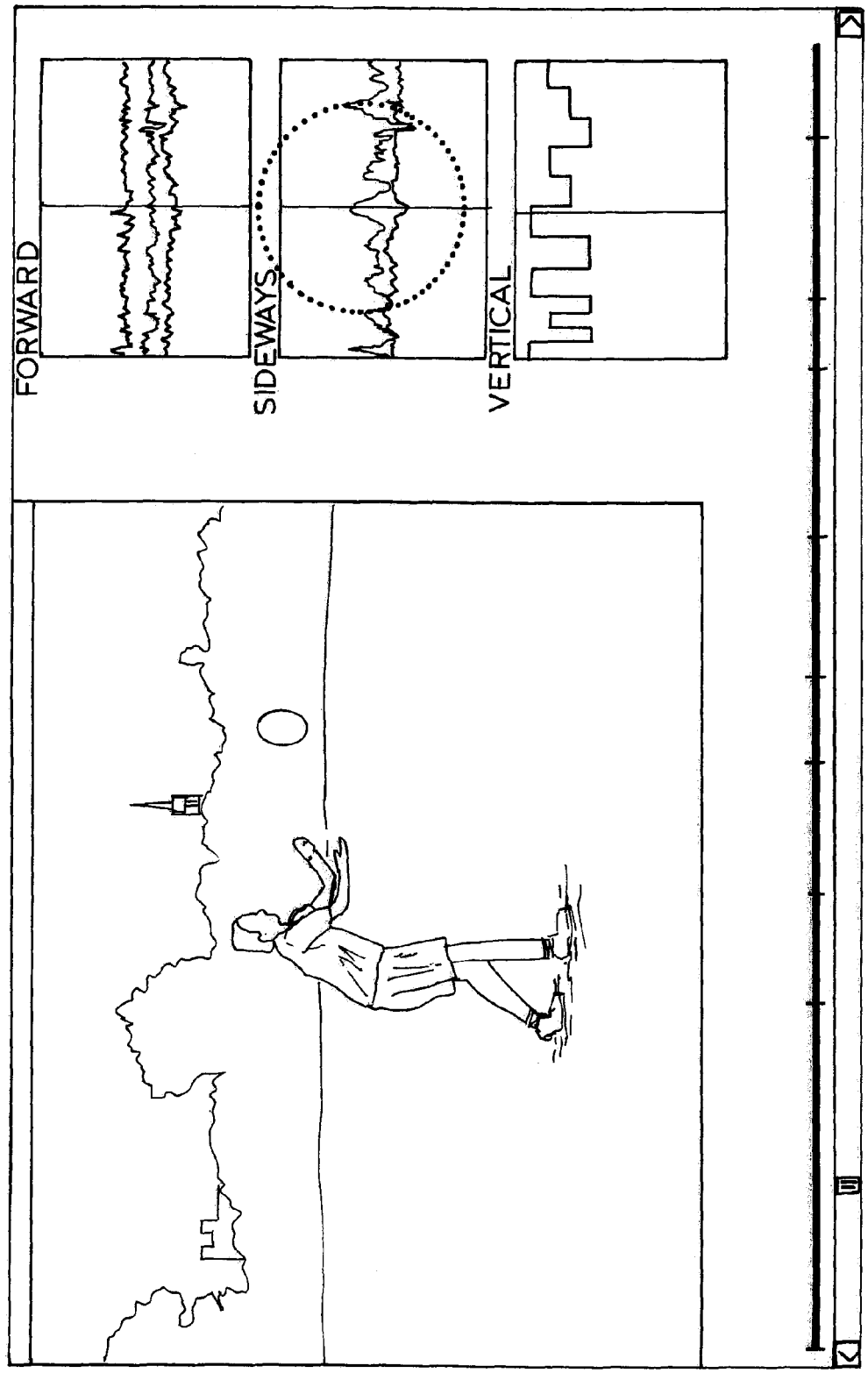
Figure 16:
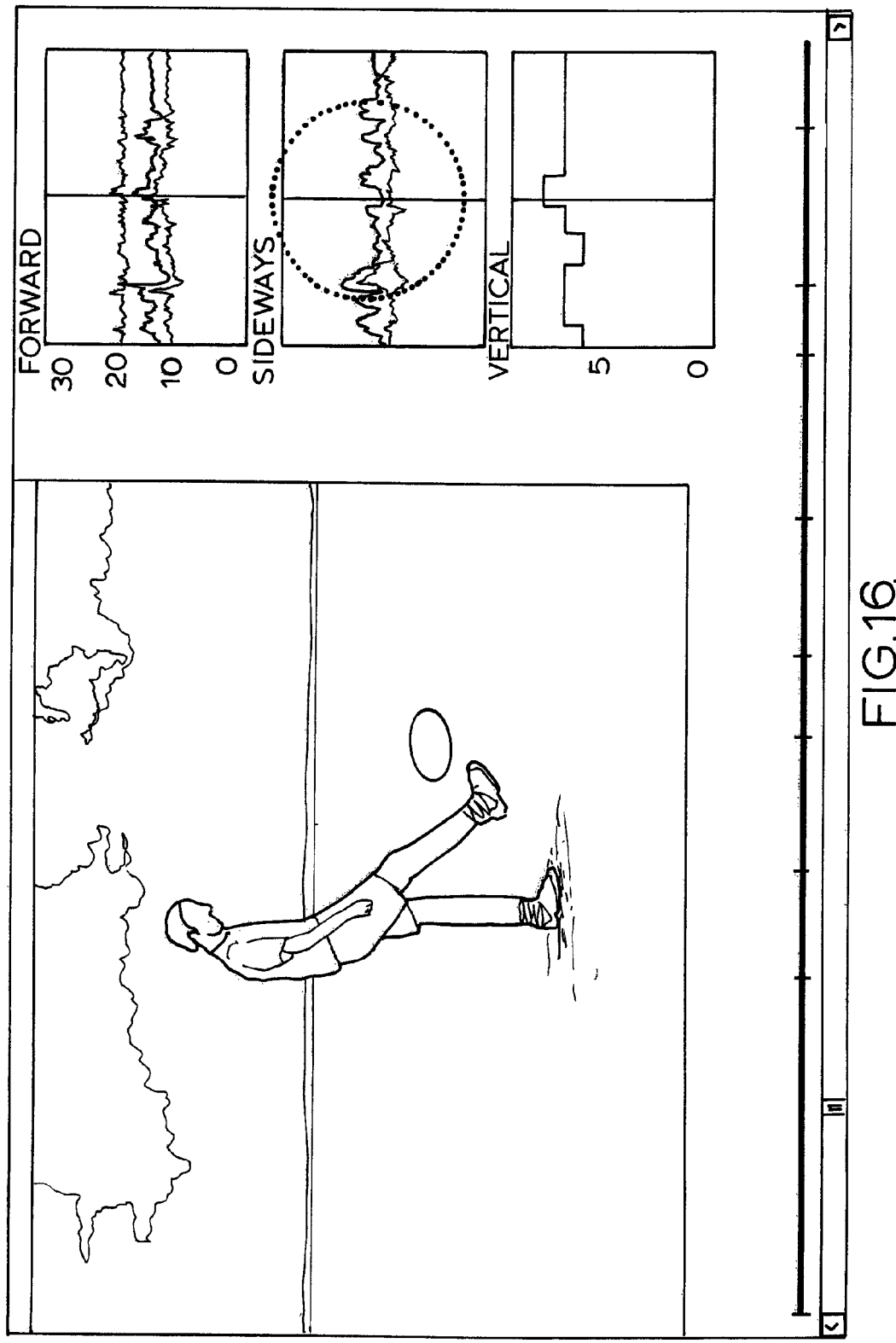

FIG. 6 the core circuit diagram for monitor mounted on an athlete;

FIG. 7 is the radio transceiver circuit for the monitor of FIG. 6;

FIG. 8 is the sensor circuits for the monitor of FIG. 6;

FIG. 9 video frame and triaxial accelerometer readings for a runner;

FIG. 10 displays the readings of a number of sensors for a long distance run including a GPS map;

FIG. 11 is a video frame and triaxial accelerometer readings for a cross country skier;

FIG. 12 is a video frame and triaxial accelerometer readings for a snow boarder;

FIG. 13 are triaxial accelerometer readings from the device of this invention mounted on a bicycle;

FIG. 14 is a video frame and triaxial accelerometer readings for an airborne mountain bike;

FIG. 15 is a video frame and triaxial gyro readings for a an Australian rules football player handballing;

FIG. 16 is a video frame and triaxial gyro readings for an Australian rules footballer player kicking.

A rowing stroke is a precise movement with rowers using their legs, back and arms to generate power. A stroke begins with the placing of the oar in the water and ends with the reemerging of the oar from the water and positioning for another cycle. The rowing stroke can be divided into four main phases: catch, drive, finish and recovery. These sequential phases must flow from and into each other to produce a continuous and fluid movement The Catch. At the catch, the blade is placed into the water quickly while the disturbance to the boat is minimised. The rower's arms are extended outward, torso is tilted forward, and legs are compressed. A good catch produces a minimal amount of back and front splash and causes minimal check. The catches of all crew members of a boat must be identical. Out of step catches (unsynchronisation) cause balance problems and reduce a boat's speed. The blade must be fully squared to the water at the catch.

The Drive. Boat gains its speed on the drive. In this portion of the stroke, the oarsman applies power to the oar with forces from arms, back and legs, and swings his torso away from the stern of the boat. The handle of the oar is pulled in a clean, powerful and leveled motion towards the bow of the boat with a constant force.

The Finish. At the finish, the oarsman finishes applying power to the oar handle, removes the blade of the oar from the water sharply, and feathers the oar so that the blade of the oar becomes parallel to the surface of the water.

The Recovery. This portion of the stroke gives rowers a brief rest to prepare for the next stroke. The oarsman must slide towards the stern of the boat and prepare the blade for the next catch. Crews exhibit an approximate 2:1 ratio between the time spent on the recovery and the time spend on the drive. At the end of the recovery, the oar is gradually squared (the blade of the oar becomes perpendicular to the surface of the water) and prepared for the catch.

Understanding which movements should occur in each phase of the stroke allows coaches to design effective conditioning programs and evaluate rowing performance effectively. Success in competitive rowing is achieved by taking the shortest time to complete a 2000 m course which directly links to the average velocity of the boat. Acceleration is proportional to force and time since the boat is accelerated as it reacts with the sweeping arc of the oar. Three factors affecting boat velocity, power, length and rate, are important determinants of rowing performance. The power provides how fast the boat travels in a stroke, the length is associated with how far the boat travels in each stroke and the rate provides how many strokes are rowed per minute. Therefore the rower must achieve an optimal combination of high stroke power, long stroke length and high stroke rate.

Data obtained from accelerometers has been used to aid the coaching process and improve athlete performance.

Recent developments in micro-electromechanical systems (MEMS) technology have opened new avenues for the use of high precision lightweight accelerometers and gyroscopes for new and challenging sports applications (e.g. characterise rate and length of rowing stroke and stride). MEMS integrate both electrical and mechanical components on a single chip through extensive research into integrated circuit processing technologies. As MEMS accelerometers originated from monitoring vehicle safety and electronic stabilisation, they only provided very low accuracy measurements. However, as micromechanical devices are inherently smaller, lighter, and usually more precise than their macroscopic counterparts, more and more reliable sensors are becoming available. Accelerometers measure linear acceleration and gyroscopes measure angular acceleration (pitch, yaw and roll).

Inertial sensors errors include initial system heading errors, accelerometer scale factor and bias errors. These drifts and biases inherent in the inertial sensors will cause a misalignment of the platform and errors in the sensed accelerations, which subsequently results in errors in computed velocities and positions.

The advent of the advanced global navigation satellite systems (GNSS), GPS in particular, has revolutionized conventional precise positioning techniques. GPS has been made more amenable to a wide range of applications through the evolution of rapid static and kinematic methods, and now even more so with the advent of the On-The-Fly (OTF) technique and most recently network-based RTK techniques such as the Trimble virtual reference station system and Geo++ surface correction parameter method. Real-time Kinematic (RTK) or single epoch positioning allows for the determination of the integer ambiguities in real-time. It is therefore not necessary to carry out any static initialization before performing the survey. Due to the small wavelengths of the carrier phase frequencies (ëL1,Ö19 cm and ëL2,Ö24 cm), the determination of position within a specific cycle to a millimetre level by utilising differential carrier phase measurements (i.e. differential techniques) is possible. Most systems statistically determine the most likely solution for the position of the roving receiver. Virtually, all carrier phase processing algorithms that utilise an OTF technique, rely on the double difference carrier phase observables as the primary measurement. A search box is determined within which the position must lie. All possible solutions are then assessed and the statistically most-likely candidate is selected. This procedure is extremely computing intensive, particularly with a large number of satellites.

Regardless of whether the system is for real-time or post-mission use, the algorithm is generally treated the same. Clearly, with real-time implementations, data outages, unfavourable observation environments, multipath and cycle slips can severely limit the performance of the system. The time for ambiguity resolution can range from a few seconds to several minutes depending on some of the following considerations:

Use of L1 versus L1-L2 (widelane, $_{L2,}$Ö 86 cm) observable
Distance between reference and roaming receivers
Number and geometry of satellites
Ambiguity search method used and differential atmospheric conditions
Quality of the received signal (multipath effects, code and carrier phase noise etc.)

Precise detection and removal of cycle slips is essential for the successful use of the OTF kinematic GPS technique. Various cycle slip detection techniques have been developed in the past decade. Included are double and triple differencing techniques, comparing the difference between adjacent carrier phase and code values (range residual), comparing the adjacent four observables equation, comparing adjacent ionospheric residual, the least-squares ambiguity decorrelation adjustment, carrier phase curve fitting, using redundant satellites and using the raw Doppler values. These methods typically assume a known stochastic behaviour for un-modelled errors (e.g. noise, multipath, differential atmospheric effects), which if present, will adversely affect the performance of the algorithm. None of these techniques can "cure all" kinematic positioning problems. Sometimes a cycle slip may be detected, but not accurately corrected for. Such instances include a loss of lock, large multipath effects and lower signal-to-noise ratio. This necessitates the combination of two or more of these techniques for a more robust solution.

Figure 1:
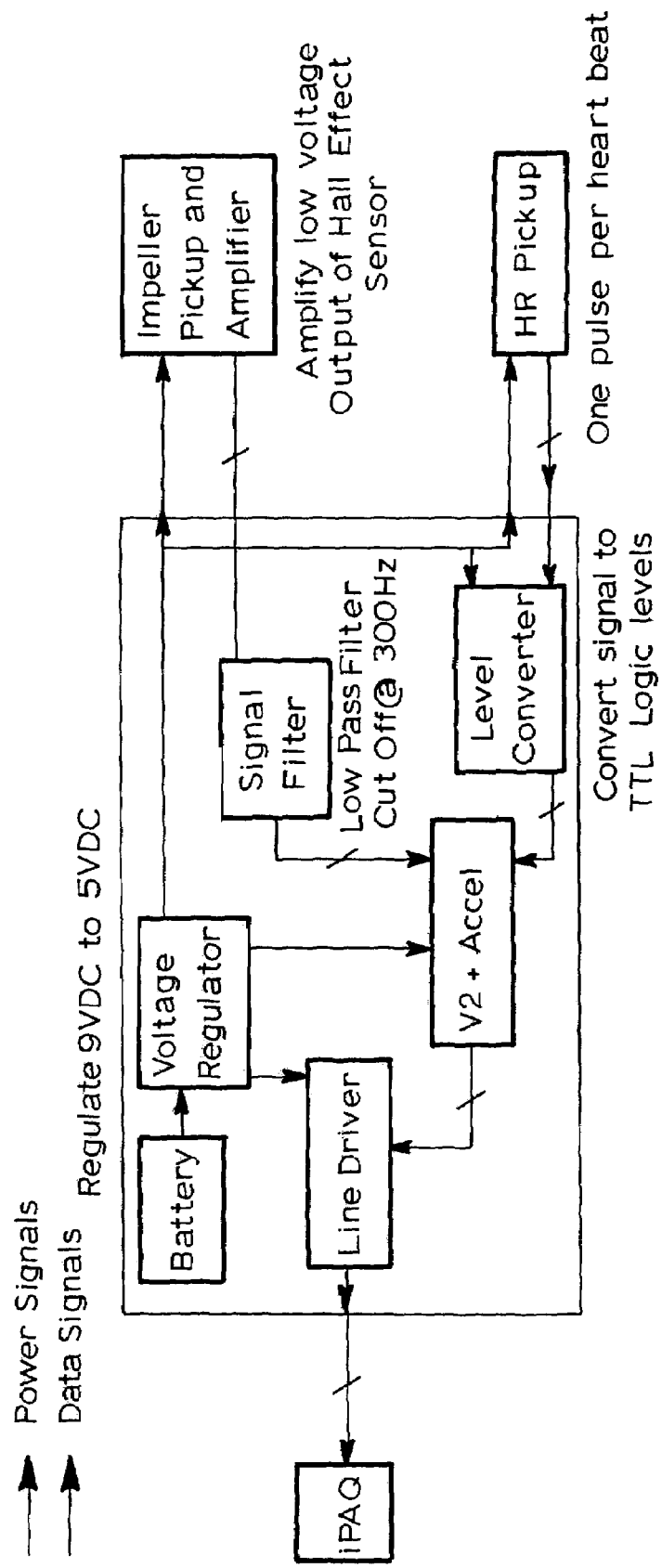
FIG. 1 is a schematic layout of a data logger used for a rower and a rowing shell.

FIG. 1 illustrates the basic components of a system to monitor boat speed and an oarsman's heart rate.

The accelerometer provides a PWM output where the duty cycle is related to the acceleration. On the rising edge and falling edge of the PWM output, a timer value is captured and used to calculate the accelerometers duty cycle. The firmware also includes an algorithm to adjust for jitter in the PWM period, and for a small amount of drift. A more detailed algorithm that compensates for temperature drift over time has been looked at, and will be implemented at a later date.

The impeller pickup uses a Melexis MLX90215 Hall Effect sensor to detect the rotations of the NK impeller. The MLX90215 is programmed with a sensitivity of 100 mV/mT. Output from the sensor is amplified by 100 to increase the signal amplitude to a usable range. This signal is then sampled using an A/D at 1200 Hz and processed using DSP techniques within the firmware to calculate rotations. Instead of using an impeller to detect boat speed a water flow sensor may be used. One preferred sensor is a micro PCB or silicon based micro fluid flow sensor that uses a heater in combination with a heat sensor that measures the change in temperature of fluid flowing past the heater and sensor to determine the fluid flow rate which in this case is the water flowing past a fixed point on the boat hull. This can then be used to measure boat speed.

For competition and race profile analysis it is preferred not to use impellers or water flow sensors but rely on GPS and accelerometers.

The display device is a handheld Compaq iPAQ™ computer programmed to present the data in a form that is useful to a coach or rower.

It is preferred that the device have data logging and IrDA transfer capabilities which makes data storage on the unit of slightly less importance. However storing data on the unit makes sense as the raw data can be streamed into the device and the greater processing power of the unit chip allows for flexible software and display development.

The microprocessor is a Hitachi HD64F3672FP which stems from the H8/300H family. Its main features are:
eight 32-bit registers OR sixteen 16-bit or sixteen 8-bit
Serial communication Interface (SCI)
10-bit ADC (4 channels)
2 k bytes of RAM The accelerometer unit is powered from a 9 Volt battery, which is regulated down to 5 volts internally. The dimensions of the accelerometer unit are 25 mm×30 mm×9 mm (smaller that the average matchbox). The cover needs to be splash proof but importantly the on/off buttons and start/stop buttons etc must be able to be accessed even when the rowers are wearing gloves.

All the chips that have been selected are amongst the smallest available in their range, the Hitachi HD64F3672FP measures on 12 mm×12 mm, this incorporates a 64 pin architecture and the ADXL202 measuring only 5 mm×5 mm.

Figure 2:
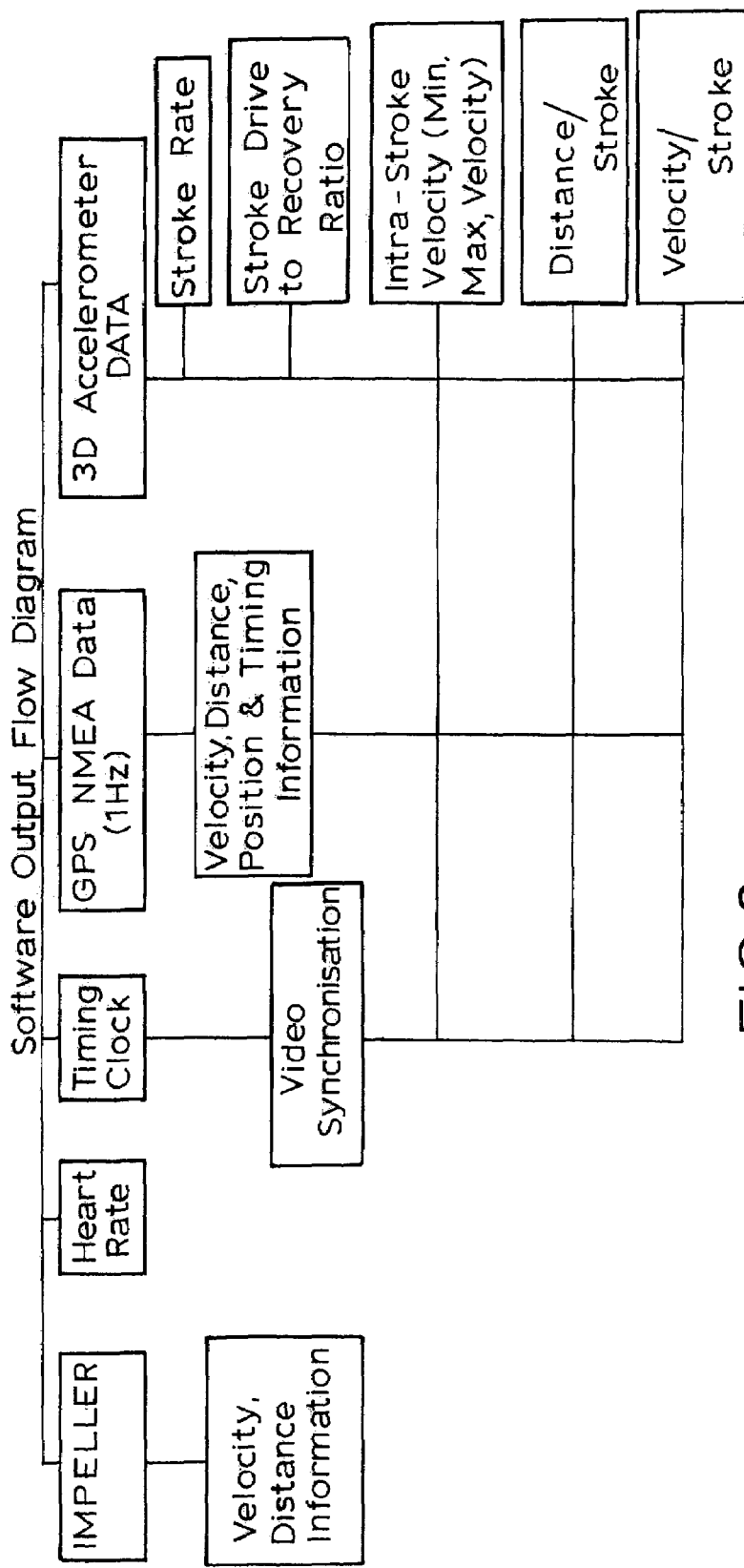
FIG. 2 shows the software output flow diagram for a rowing data logger.

FIG. 2 illustrates the output flow from the various sensors namely impeller, heart rate monitor, clock, GPS sensor and 3 D accelerometer. Stroke rate and stroke drive to recovery ratio are most conveniently derived from the accelerometer data while intra stroke velocity, distance per stroke and velocity per stroke are derived from the accelerometer, GPS and time clock data.

The data for 1 block (by 3 or 4 channels) will be packaged and transmitted in a single frame. The sampling time for a frame (1 block at 150 samples/sec) will be equivalent to 6.6 ms. This data will be combined with block and channel information.

A total of eight bytes is required to transmit one block of data this includes the header, two 16-bit channels, Impeller Rotation count and Heart Rate count. The Heart Rate count is only transmitted once a second, or one in every 150 frames. Heart rate is an output indicating the millisecond value from the previous beat or the millisecond of the beat that occurred during that packet of information. This is used to calculate instantaneous HR on a beat to beat basis. Alternately the number of beats in 15 secs is totaled and then multiplied by 4 to get the HR. The algorithm then runs on a 5 sec rolling average to smooth the data. Given that maximum HR will never exceed 250 bpm this means that at most a beat will occur every 240 ms which is approximately 1 pulse every 2 packets of information. Table 1 shows a block of data excluding the framing and network information data.

TABLE 1

| Byte | |
|---|---|
| 1 | Frame header(xEE) |
| 2 | Number of Blocks(4 bits) |
| | Number of channels (4 bits) |
| 3 | ACC "Y" bits 1-8 |
| 4 | ACC "Y" bits 9-16 |
| 5 | ACC "X" bits 1-8 |
| 6 | ACC "X" bits 9-16 |
| 7 | Impeller rotation count (8 bits) |
| 8 | Heart rate count (8 bits) |

Table 2 illustrates an example of the bit stream for 2 frames. The first frame containing two 16-bit channels and Impeller Rotation count, and the second frame containing two 16-bit channels, Impeller Rotation count and Heart Rate count

TABLE 2

| Data Stream | Meaning |
|---|---|
| 0xEE | Header Byte |
| 0x13 | One Block, eg. 3Channels |
| 0xA9 | Acc Y Lower Byte |
| 0xEA | Acc Y Upper Byte |
| 0x46 | Acc X Lower Byte |
| 0xC9 | Acc X Upper Byte |
| 0x01 | Impeller Rotation Count |
| 0xEE | Header Byte |
| 0x14 | One Block, eg. 4Channels |
| 0xA9 | Acc Y Lower Byte |
| 0xEA | Acc Y Upper Byte |
| 0x46 | Acc X Lower Byte |
| 0xC9 | Acc X Upper Byte |
| 0x01 | Impeller Rotation Count |
| 0x02 | Heart Rate Count |

A single unit may be used for each crew member or the heart rate lines for each crew member can be included with the accelerometer and speed data to provide a composite set of data. In a multi crew boat each crew member has a receiver within 2 feet that picks up the heart rate signal from the polar heart rate monitor strapped to each crew member. Each heart rate monitor transmits a uniquely coded signal that is assigned to each crew member. The boat data logger receives the heart rate signals for all crew members by cable from the heart rate receivers A GPS unit may be integrated with the data logger system. This could comprise two units, basic unit plus a second unit for GPS. The units would share the same serial line and communicate using a network protocol. Alternatively the GPS unit could be connected to the basic unit and additional firmware code added to receive and retransmit data.

Inertial navigation systems (INS) may be used to cover the information gaps of the GPS outages. When the INS approach is used in rowing, the required sensors need to be small, lightweight, unobtrusive and inexpensive. These requirements can be met when the sensors are manufactured with MEMS technology. However, due to inherent biases and drift errors of accelerometers and gyroscopes, the accuracy of the current state-of-the-art MEMS sensors must be accounted for in high precision rowing tracking. The basic procedure in INS positioning systems is to process the inertial sensor data. The double integration of acceleration measurements, cannot be applied due to the lower accuracy of MEMS sensors. This is because in the double integration, errors accumulate quickly, which soon result in velocity errors comparable to typical rowing speeds. However, the advantages of the INS system include its low cost and high output rate of the movement information.

The high precision GPS system can provide high precision velocity and acceleration information (acceleration is the first derivative of velocity and second derivative of displacement). However the GPS system is normally bulky, expensive and provides a low output rate and high power consumption. To solve these problems, an integrated system takes advantage of both low-cost GPS and MEMS sensors to provide high performance capabilities. MEMS sensors are used to provide precise, high rate (say 200 Hz), low cost, low volume, low power, rugged, and reliable geo-positioning while low-cost GPS may be used for high frequency system calibration (say 5-20 Hz) a lower frequency (1 Hz) is preferred for calibrating the inertial sensors to conserve battery power. It combines measurements from a GPS OEM board and subsequently GPS chip with inertial measurement units from a combination of three MEMS gyroscopes and accelerometers (say Analog Devices).

A 1 Hz GPS receiver is the minimum frequency that is practical and ideally a 2-5 Hz system is preferred. With a 1 Hz receiver accurate velocity and distance measurements can be obtained but sampling the accelerometer data is needed to obtain stroke rate and intra-stroke characteristics. The accelerometer data could be integrated to get intra-stroke velocity but drift would need to be checked every second using the output from the GPS receiver.

The carrier smoothing procedure will be used to improve the accuracy of the low-cost GPS pseudo range measurements. Carrier phase smoothing is a process that the absolute but noisy pseudo range measurements are combined with the accurate but ambiguous carrier phase measurements to obtain a good solution without the noise inherent in pseudo range tracking through a weighted averaging process. A Kalman filtering system will be designed to integrate the two system measurements.

Figure 3:
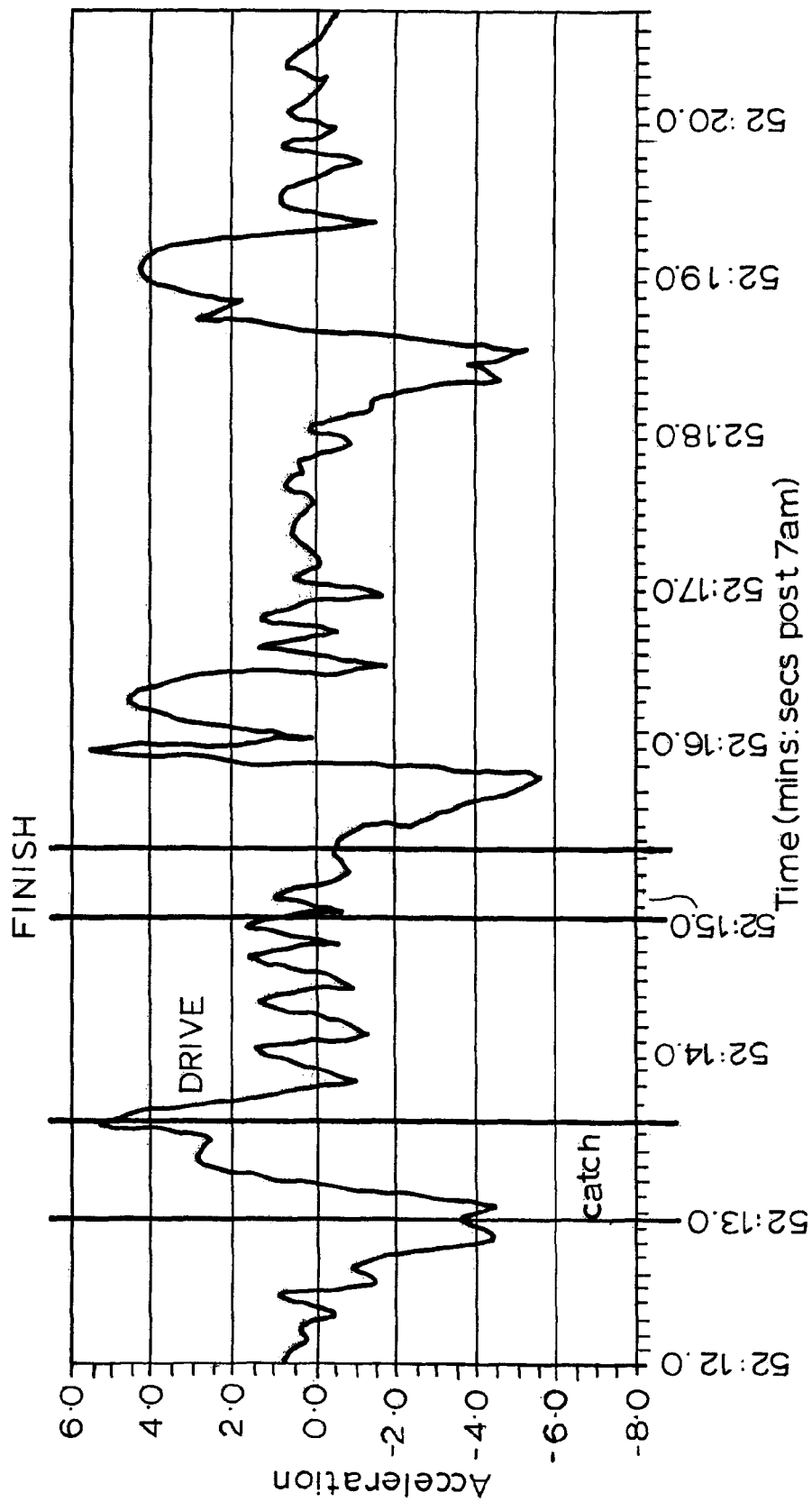
FIG. 3 is a graphical illustration of stroke determined by using GPS data.

FIG. 3 presents the stroke signals captured using geodetic type GPS receivers and post-processing with the kinematic differential GPS technique. It is demonstrated that the signals captured provide a clear picture of the rowing stroke phases as described above. In this particular stroke, the graph indicates that the rower has problem in harmonising his stroke cycle by using too much time in the catch instead of the driver.

Figure 4:
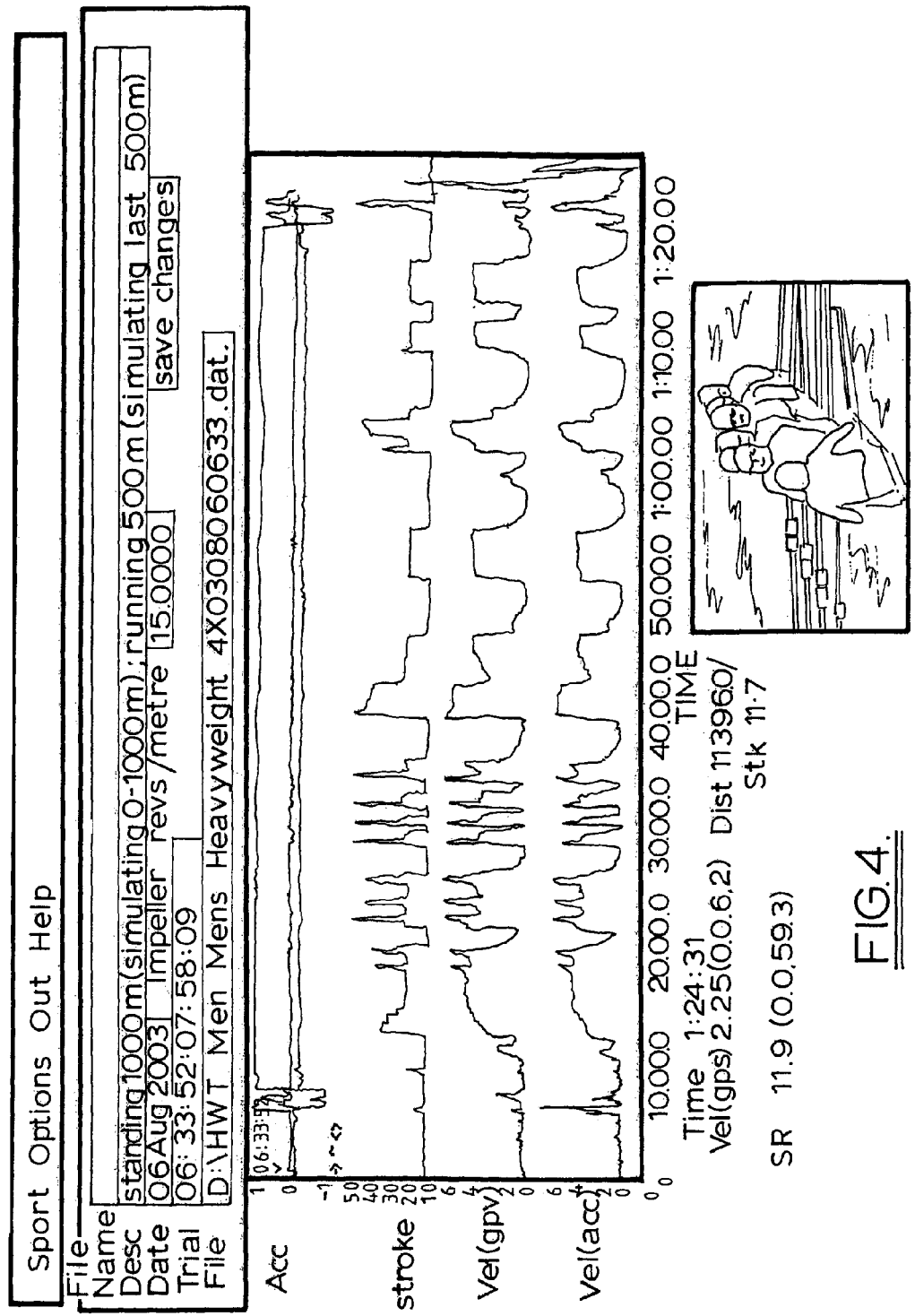
FIG. 4 illustrates the display for a computer screen.

The software can display the derived information on a computer screen and combine it with video data of the same event as illustrated in FIG. 4. The screen may display time and distance information as well as velocity and stroke rate and can also display the graphical signals derived from accelerometer and GPS signals.

To evaluate the accuracy of the GPS carrier phase receiver, two GPS receivers were mounted on the same rowing boat simultaneously. The base station is located on the bank of a river which is about 1~2 km away from the course of the boat trial. The baseline solutions from each of the rowing antennas were processed independently from the base station using the PPK technique. The independent baseline length between the two roving receivers was then calculated and compared with the result measured using a surveying tape. This baseline length is considered as a "ground truth" (3.57 m in our case). RTK GPS has been proved to be able to provide high precision positioning in river environment. However, there are a number of factors that need to be taken into consideration:

Multipath effects: The antenna being positioned near the water surface could potentially be prone to large multipath error. This effect can be up to 5 cm for carrier and 5 m for code measurements respectively.

Signal obstruction/satellite visibility: The GPS antenna is installed in a constricted space in a racing boat, it is therefore unavoidable that the movement of the athlete will block the GPS signals at some time to an elevation angle of approximately 70 degrees. This may potentially cause severe signal obstruction problems and loss of GPS solutions.

Obtrusion: Ideally the presence of any instrument should not cause direct visual or physical impact on the athlete, therefore, the size and height of the antenna is a primary consideration.

The "fixed baseline length" and external check methods are used. Reliable mounting of the GPS receiver is required. If we assume that the accuracy of the position to one GPS rover is the same as to the other, then, from the simple (Least Squares Adjustment) error propagation law, the accuracy of the position of the kinematic GPS measurement (for a single baseline) can be estimated as 0.0027 m (0.0038 m/sqrt(2)). A few millimetre accuracy of the river height was achieved in a three (consecutive) day trial. Given the closeness of the antenna and the reflective nature of the water surface, the performance of the PPK GPS presents consistent results.

The velocity determined from the GPS position and time information uses the following first-order central difference procedure.

$$\text{Velocity}(v_T) = \frac{P(T+\Delta T) - P(T-\Delta T)}{2\Delta T} = \frac{\Delta P}{2\Delta T}$$

where $v_T$ is the velocity of the boat (at time T) determined from PPK GPS solution, $\Delta P = P(T+\Delta T) - P(T-\Delta T)$ is the plane distance traveled between time $T_1$ and $T_2$ and $\Delta T = T_2 - T_1$. $\Delta P = \sqrt{(N_2-N_1)^2 + (E_2-E_1)^2}$, where E and N are the Easting and Northing coordinates of the GPS units. The subscripts "1" and "2" indicate that position derived from unit 2 and unit 1 respectively. The accuracy of the velocity ($\sigma_v$), can then be roughly estimated through the following formula (using the error propagation law):

$$\sigma_v = \frac{1}{\sqrt{2}\,\Delta T}\sigma_P = \frac{1}{\sqrt{2}\times 0.1}\cdot 0.0027 \approx 0.02 \text{ m/s}$$

Where $\sigma_P$ is the positional accuracy and $\sigma_P = 0.0027$ m as determined previously.

Figure 5:
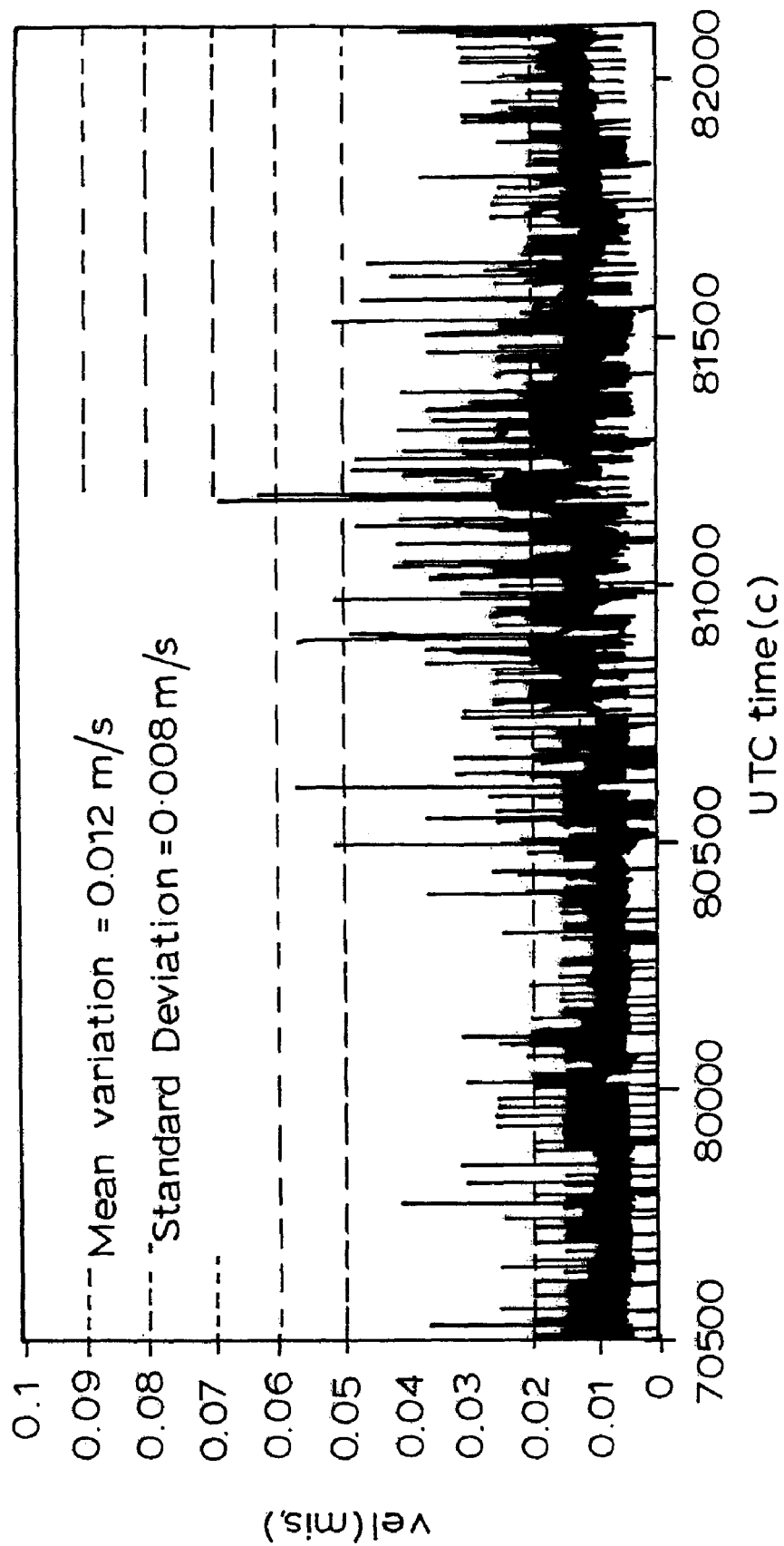
FIG. 5 illustrates the deviation between code and carrier derived velocity measurements.

FIG. 5 shows the differences in velocity determined simultaneously from the code and the carrier measurements. Assuming the carrier velocity to be accurate (ie ground truth), the code derived velocity has an average accuracy in the order of ~0.03 m/s. The results confirm that the accuracy of 0.1 m/sec claimed by the manufacturer is correct for more than 95% of observations.

The data logger assembly is fitted to a rowing shell in a stable location with a relatively clear view of the sky. Relative motion of the athlete or boat is measured using three dimensional accelerometer at 100 hHz and position and velocity using GPS at 10 Hz. The device supplies timing information with the measured signals using an internal crystal corrected clock and a GPS derived 1 Hz pulse. The timing is accurate to 0.1 sec per hour. An internal heat rate monitor pickup receives pulses from a coded polar heart rate monitor/transmitter and stores these with a resolution of 1 beat a minute within a range of 0 to 250 beats/minute updated at 1 Hz. The device is powered by a battery sealed into the unit and is rechargeable via an RS232 port. Recording battery life is 6 hours and 1 month in sleep mode. The single universal port allows recharging, connecting an RF module, connecting an external GPS antenna, connecting the external heart rate receiver and to connect a serial cable to send data to the hand held computer device. The device can be fitted into a flexible package of a size approximately 100 mm×70 mm×50 mm and weighs less than 250 g and is buoyant and water resistant. The package is coloured to reduce heating from incident sunlight.

FIGS. 6 to 8 illustrate the circuitry used in further embodiment of the invention. FIG. 6 shows the core circuitry centred on the micro controller 20. The micro controller is preferably an 8 bit Atmel AT mega 128 micro controller. The micro controller can be programmed and can store data and is provided with a 256 megabyte flash memory 27. The USB port 22 is preferably a Silicon Technologies USB to UART data transfer CP 2101 and allows data to be down loaded to a personal computer for further analysis and storage and also allow the battery to be charged by way of the battery charger 31 which in turn is connected to the power supply 32. The microcontroller functions are actuated by the tactile switches 23 which allows the user to navigate through the device menu. The microcontroller displays outputs on the LCD display 35 and also provides a backlight display 36. As shown in FIG. 7 the monitor includes a 2.4 GHz transmitter and receiver 40 so that data can be transmitted and received. The transmitter and receiver 40 see is preferably a GFSK transceiver nRF2401 sold by Nordic Semiconductor. The output power and frequency channels are programmable using a 3 wire serial interface. The GPS unit is an iTRAX 03 by Fastrax with 12 channels and an update rate below 5 Hz with a 1 Hz default rate.

The sensor circuits shown in FIG. 8 are the core components of the real time clock 41 the three axis accelerometer 43. A single external transistor may be used to lower the scale factor and an external capacitor is used to set the bandwidth.

A display is mounted in a water proof enclosure in a visible location so that the athlete can view summary information such as speed, distance and heart rate. An easily accessible button on the display unit starts the data recording. As soon as the device is switched on recording begins. The coach may take the device after the event and load the data into a personal computer to view the data graphically or combine it synchronously with video footage.

For athletics or skiing the device is attached to an athlete near the small of the back but may also be attached to the ankle adjacent the Achilles tendon or to the shoe or ski. An extension GPS aerial runs from the device to the shoulders or other convenient point. A similar location is also suitable for swimming although mounting on the wrist or head is also possible.

In cycling the device may be worn by the rider or mounted on the handlebars of the bike for easy visibility. The pedal cadence can be deduced from the accelerometer data but may be collected from a cadence sensor either wired to the monitor or sent by a wireless blue tooth arrangement.

The RF module enables the real time data to be transmitted to the Coach's wireless enabled PC via a blue tooth connection. Alternatively the data may simply be uploaded after the event.

As shown in FIGS. 9 to 16 the device can be adapted for a wide range of sports. Analysis of the signals from the 3 axes of the accelerometer allows coaches to derive information as detailed stride length and variations in the push from each leg of a runner as shown in FIG. 9. For long distance training session the data from a group of sensors can be presented as shown in FIG. 10 in which the first frame shows the 3 axes of the accelerometer; the second frame shows the velocity as derived with the assistance of the GPS sensor; and the third frame contains the altimeter readings over the course. On the right hand side the GPS plot of the overall course is shown.

In skiing as shown in FIG. 11 analysis can show the power derived from each leg thrust or pole thrust.

In snow boarding (FIG. 12) loft time and speed can be derived from the data. This uses the accelerometer data to determine the lift off point and the return point to determine the air time.

One algorithm according to this invention is designed to show air time and total angular movement during the "air". To detect the air it uses three parameters which are available at 100 Hz—forward/backward acceleration, up/down acceleration and ac3diff. The first two parameters are filtered through a 2 pass Butterworth filter with a 2.5 Hz cutoff. Each ac3diff value is the square root of the sum of the squares of the differences between adjacent triaxial accelerometer readings and is an indicator of activity. This algorithm first looks for the end of an "air" which is indicated by a large spike in ac3diff at landing. The spike must have 5 out of 6 ac3diff readings each at least 0.05 greater than the previous reading. The spike must also rise by at least 0.5 over the 6 readings and must be at least 0.7 secs after the end of the previous "air". The algorithm then looks back for the beginning of the "air" in the 0.3 to 2 seconds range. This is defined as a peak in upward acceleration with a steep approaching slope (10 of 20 points at least 0.03 g above previous point). There must also be a similar steep drop in forward/backward acceleration.

The readings from a triaxial accelerometer and GPS mounted on a bike are shown in FIG. 13. Cadence and gear changes can be seen from the forward acceleration and velocity changes. This can be measured using the accelerometers and correcting with GPS. Altimeters can be included for bikes. By computing real forward acceleration the power can be measured. Thus the rider can see on the bike display distance, velocity, cadence and power.

FIG. 14 illustrates airtime in a mountain biking event. In mountain biking, the device of this invention can separately analyse the various sections of the course and identify uphill, downhill, flat technical and non technical sections. This is also applicable to cross country skiing and running.

In football codes the combination of gyro and accelerometer sensors enables hand balls and kicks to be detected. The algorithm looks for a peak in the pitch gyro (4 gyro readings increasing by 4 degrees per sec followed soon after by 4 decreasing by 3 deg/sec over a period of between 130 and 350 ms. The first reading must be less than −90 deg/sec. FIG. 15 illustrates a short distance handball by the left hand from a stationary position. FIG. 16 illustrates a short distance kick by the right foot from a stationary position.

Those skilled in the art will realize that the invention may be implemented in a variety of embodiments depending on the water craft used and the number of personnel in the water craft. A variety of sensors may also be used to gather data applicable to the event and the water craft. It will also be appreciated that the logger unit is small and adaptable enough to be fitted to any athlete or sporting equipment where accelerometer data provides useful performance information for coaches and athletes. These include athletics, swimming, team sports such as various football codes, cycling and skiing.

The invention claimed is:

1. A data acquisition system for use in sporting events which incorporates
    a) a global position sensor to derive three dimensional positioning data relative to time elapse
    b) at least one accelerometer to derive acceleration and velocity data in three dimensions
    c) a microcontroller with a clock to interrogate the global position sensor and to collect the accelerometer data
    d) a power supply
    e) means for transmission of global position and accelerometer data from the microcontroller to a computer device
    f) the computer device being programmed to use the global position and accelerometer data to provide accurate and continuous output of parameters such as velocity acceleration and distance traveled.

2. A data acquisition system as claimed in claim 1 in which velocity is derived from the global position sensor and the accelerometer data is sampled to obtain movement characteristics of the sport being monitored.

3. A data acquisition system as claimed in claim 1 wherein the accelerometer data is integrated to derive velocity related movement characteristics and drift is be checked every second using the output from the global position sensor.

4. A data acquisition system as claimed in claim 1 wherein an inertial navigation system based on the accelerometer data is used to determine position when the GPS system is unable to receive it data.

5. A data acquisition system as claimed in claim 1 which also includes a physiological sensor.

6. A data acquisition system as claimed in claim 5 in the physiological sensor is a heart rate monitor.

7. A data acquisition system as claimed in claim 6 for a cyclist which also includes a pedal cadence sensor.

8. A sports data acquisition system which incorporates
    a) at least one accelerometer to derive acceleration, and velocity data in three dimensions
    b) a microcontroller with a clock to collect the accelerometer data
    c) a power supply
    d) means for transmission of the accelerometer data from the microcontroller to a computer device
    e) the computer device being programmed to use the accelerometer data to provide accurate and continuous output of parameters such as air time and velocity.

* * * * *